US00PP18192P2

(12) United States Plant Patent
Fairweather

(10) Patent No.: US PP18,192 P2
(45) Date of Patent: Nov. 13, 2007

(54) ***ROSMARINUS* PLANT NAMED 'ROMAN BEAUTY'**

(50) Latin Name: *Rosmarinus officinalis*
Varietal Denomination: ROMAN BEAUTY

(76) Inventor: Christopher Fairweather, Hill Top Nursery, Beaulieu, Hants SO42 7YR (GB)

( * ) Notice: Subject to any disclaimer, the term of this patent is extended or adjusted under 35 U.S.C. 154(b) by 23 days.

(21) Appl. No.: 11/294,704

(22) Filed: Dec. 5, 2005

(51) Int. Cl.
*A01H 5/00* (2006.01)

(52) U.S. Cl. ..... Plt./226

(58) Field of Classification Search ..... Plt./263, Plt./226

See application file for complete search history.

*Primary Examiner*—Kent Bell
*Assistant Examiner*—S. B. McCormick-Ewoldt

(57) ABSTRACT

A new and distinct cultivar of *Rosmarinus* named 'ROMAN BEAUTY' that is characterized by compact upright habit, mid-green foliage and violet-blue flowers. In combination these traits set 'ROMAN BEAUTY' apart from all other existing varieties of *Rosmarinus* known to the inventor.

2 Drawing Sheets

Genus: *Rosmarinus*. Species: *officinalis*.
Denomination: 'ROMAN BEAUTY'.

BACKGROUND OF THE INVENTION

The present invention relates to a new and distinct cultivar of rosemary that is grown as an ornamental for containers or landscape. The new cultivar is known botanically as *Rosmarinus officinalis* and will be referred to hereinafter by the cultivar name 'ROMAN BEAUTY'.

'ROMAN BEAUTY' was selected by the inventor in Beaulieu, Hants, United Kingdom in 2003 for its improved habit for ease of shipping. The new cultivar 'ROMAN BEAUTY' is a result of open pollination among a number of unnamed plants of *Rosmarinus officinalis* Prostratus Group. The seed parent is a plant of *Rosmarinus officinalis* Prostratus Group. The pollen parent is unknown.

'ROMAN BEAUTY' is a dwarf perennial ground cover characterized by a compact habit, mid-green foliage, and violet-blue flowers. As an immature, first year plant, the stems of 'ROMAN BEAUTY' are faintly tinged with red. As the plant ages and becomes mature, the stems become woody and gray-brown in color.

'ROMAN BEAUTY' differs from its shorter female parent *Rosmarinus officinalis* Prostratus Group in that 'ROMAN BEAUTY' is more upright in habit. Two close comparison plants known to the inventor are *Rosmarinus* 'Rampant Boule' (unpatented) and *Rosmarinus* 'Pointe du Raz' (unpatented). 'ROMAN BEAUTY' differs from 'Rampant Boule' in that 'ROMAN BEAUTY' has a tidier habit; and from 'Pointe du Raz' in that 'ROMAN BEAUTY' is smaller in habit, and with darker flowers.

The first asexual reproduction of 'ROMAN BEAUTY' was conducted by the inventor in a cultivated area of Beaulieu, Hants, United Kingdom in 2003. The method used for asexual propagation was vegetative cuttings. Since that time the distinguishing characteristics of 'ROMAN BEAUTY' have been determined stable and have reproduced true to type in successive generations of asexual reproduction.

SUMMARY OF THE INVENTION

The following traits have been repeatedly observed and represent the distinguishing characteristics of 'ROMAN BEAUTY'. These traits in combination distinguish 'ROMAN BEAUTY' from all other varieties of *Rosmarinus* known to the inventor. 'ROMAN BEAUTY' has not been tested under all possible conditions. Phenotypic differences might occur with variations in environmental, climatic, and cultural conditions without any variance in genotype.

1. 'ROMAN BEAUTY' is a perennial shrub suitable for use as a ground cover.
2. 'ROMAN BEAUTY' exhibits a dense compact habit.
3. 'ROMAN BEAUTY' exhibits mid green foliage.
4. 'ROMAN BEAUTY' exhibits gray-brown stems when mature.
5. 'ROMAN BEAUTY' is resistant to powdery mildew, and is heat tolerant.
6. 'ROMAN BEAUTY' exhibits short internodes.
7. 'ROMAN BEAUTY' exhibits violet-blue flowers from spring to early summer.
8. The lower lobe of the flowers of 'ROMAN BEAUTY' exhibit scalloped margins.
9. 'ROMAN BEAUTY' exhibits short flower stalks that produce inflorescences borne above the foliage.
10. A mature (second season) plant of 'ROMAN BEAUTY' measures 30 cm to 40 cm in width and approximately 20 cm in height when grown in the ground or in a 2-liter container.
11. 'ROMAN BEAUTY' is hardy to USDA Zone 6.
12. 'ROMAN BEAUTY' is propagated by tip cuttings and division.

BRIEF DESCRIPTION OF THE DRAWINGS

The accompanying color drawings illustrate the overall appearance of 'ROMAN BEAUTY', showing the colors as true as it is reasonably possible to obtain in colored reproductions of this type. Colors in the photographs may differ from the color values cited in the detailed botanical description, which accurately describe the actual colors of 'ROMAN BEAUTY'.

The drawing labeled

The drawing labeled

Figure 1:
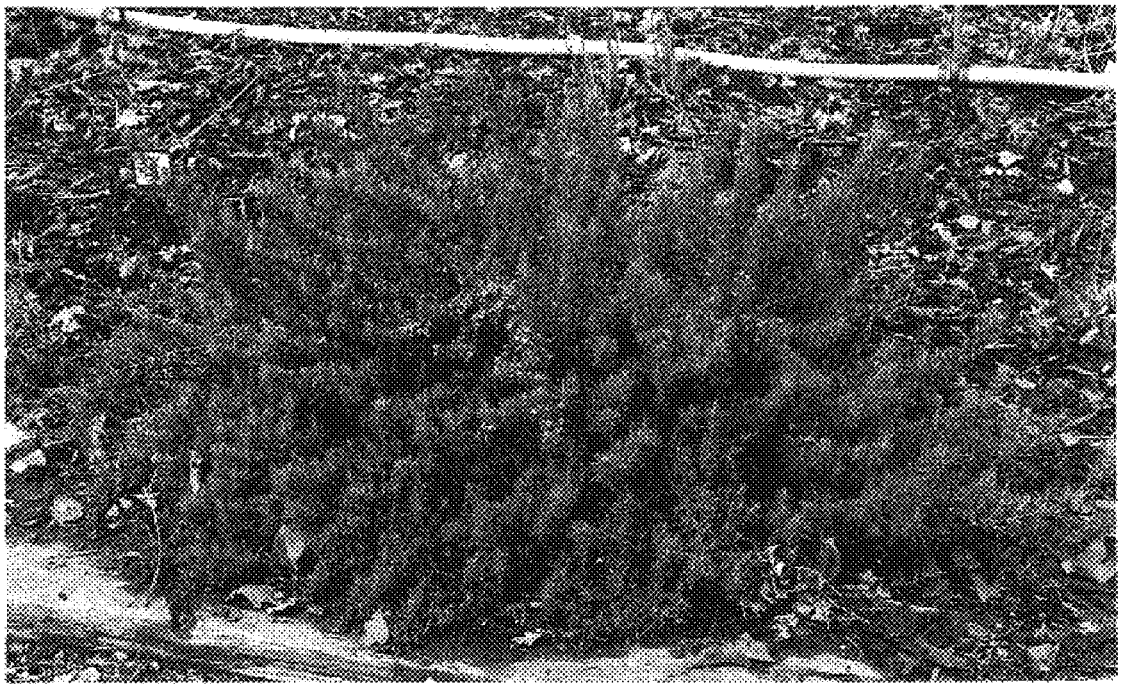
FIG. 1 illustrates an entire plant of 'ROMAN BEAUTY' which is coming into bloom in its second year of growth.
Figure 2:
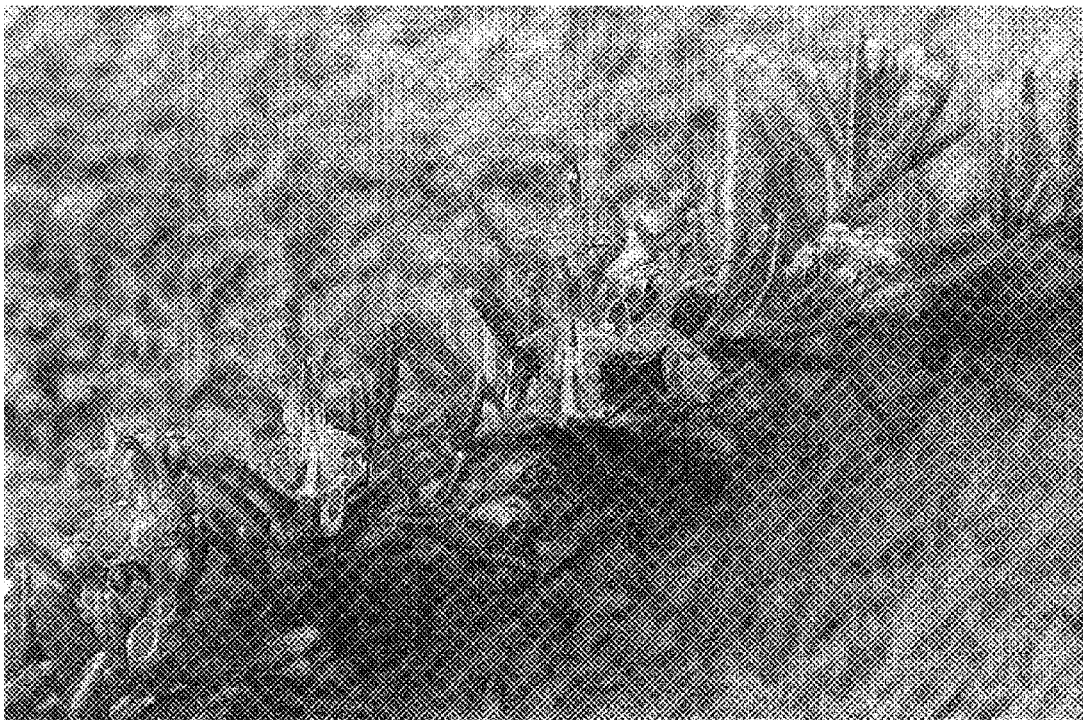
FIG. 2 illustrates a close-up view of the foliage and flowers of 'ROMAN BEAUTY'.

The drawings are made using conventional photographic techniques and although flower and foliage colors in the photographs may differ from the actual colors due to light reflectance, they are as accurate as conventional photography can portray.

BOTANICAL DESCRIPTION OF THE PLANT

The following is a detailed botanical description of 'ROMAN BEAUTY'. Observations, measurements, values and comparisons were collected in Beaulieu, Hants, United Kingdom from plants in their second season of growth in 2-liter containers that were grown out-of-doors in a frost-free environment. Color determinations are made in accordance with 2001 Edition of the Colour Chart of The Royal Horticultural Society, London, England, except where general color terms of ordinary dictionary significance are used. The growing requirements of the new variety are similar to the species and there are no growing problems known to the inventor.

Botanical classification:
- *Genus.*—*Rosmarinus.*
- *Species.*—*officinalis.*
- *Denomination.*—'Roman Beauty'.

Commercial classification: Perennial shrub.

Use: Borders and patio containers.

Common name: Rosemary.

Commercial container size: 1 gallon or 2 liters.

Cultural requirements: Plant in full sun to partial shade in well-drained soil.

Parentage: 'ROMAN BEAUTY' is a hybrid plant that resulted from the cross-pollination of the following parents:
- *Seed parent.*—*Rosmarinus officinalis* Prostratus Group.
- *Pollen parent.*—Unknown.

Plant description:
- *Blooming season.*—Spring.
- *Vigor.*—Slightly less vigorous than the prostrate rosemaries.
- *Dimensions at maturity.*—30 cm to 40 cm in width and approximately 20 cm in height.
- *Plant habit.*—Forming a dense, flattened mound with arching stems.
- *USDA hardiness zone.*—Zone 6.

Propagation method: Softwood cuttings.
- *Rooting habit.*—Fibrous.
- *Time required to develop roots on an initial cutting.*—4 weeks.
- *Recommended air temp for cutting to develop roots.*—20° C.
- *Time required for a rooted cutting to reach commercial size.*—9 months in 13 cm pots.
- *Susceptibility or resistance to pests and diseases.*—None which are specific to this variety.

Stem:
- *Immature plant, one year old.*—Color: Yellow-Green 146D, faintly tinged with red (too weak to match) where exposed to strong light. Cross-section: Circular. Dimensions: Length 225 mm, diameter 3 mm. Surface: Densely pubescent. Color of pubescence: Nearest to White N155A. Lenticels: Absent. Internode length: 10 mm.
- *Mature plant, two years old.*—Color: Grey-Brown 199A. Texture of bark: Fibrous, longitudinally fissured. Presence of lenticels: Absent. Diameter: 10 mm. Branching habit: Freely branching from the base and higher up. Branch angle at emergence: Approx 45°, soon arching over.

Foliage:
- *Type.*—Evergreen.
- *Leaf.*—Shape: Linear. Dimensions: length 17 mm, width 2.5 mm. Arrangement: Opposite. Margins: Strongly revolute. Division: Absent. Apex: Obtuse. Base shape: Cuneate. Color (abaxial surface): Between Green 137B and Yellow-Green 147B. Color (adaxial surface): White 155C (due to pubescence). Pubescence (abaxial surface): Very sparse. Pubescence (adaxial surface): Very dense. Texture (abaxial surface): Rugose. Venation: Pinnate. Vein color (abaxial and adaxial): Veins indistinguishable in color from lamina. Fragrance: Strongly aromatic.
- *Petioles.*—Absent.
- *Stipules.*—Absent.

Flower:
- *Flowering season.*—April and May.
- *Arrangement.*—Flowers produced in compressed cymes in leaf axils of 1-year old stems.
- *Number of flowers per cyme.*—5–8.
- *Flower greatest overall length.*—9 mm, i.e. as corolla.
- *Flowers persistent or self-cleaning.*—Self-cleaning.
- *Flower type.*—Strongly zygomorphic.
- *Flower shape.*—Two-lipped calyx, from which projects a two-lobed corolla enclosing two exserted stamens.
- *Flower aspect.*—Horizontal.
- *Flower fragrance.*—None detectable — possibly masked by strong leaf fragrance.
- *Peduncle.*—Dimensions: Length 3 mm, diameter <1 mm. Color: Nearest to Green 138A. Surface: Densely pubescent.
- *Pedicel.*—Dimensions: Length 2 mm, diameter <0.5 mm. Color: Nearest to Green 138C. Surface: Densely pubescent.
- *Bud.*—Shape: Obovate. Dimensions: Length 7 mm, diameter 3 mm. Color: Between Violet N88C and N88D.
- *Calyx.*—Shape: Campanulate. Dimensions: Length of tube 2.5 mm, diameter of tube 2 mm. Number of lobes: 2. Length of lobes: 1.5 mm. Width of lobes: Upper lobe 2 mm, lower lobe 1.5 mm. Shape of lobes: Triangular. Shape of tip of lobes: U pper lobe obtuse, lower lobe bifid, both parts acute. Pubescence and type: Densely pubescent. Color: Green 138D but paler, faintly tinged with purple (too pale to color match) on the center of the upper lobe. Margin: Entire.
- *Corolla.*—Number of petals: Petals not clearly distinguishable; corolla divided into an upper and lower lobe, the latter having two lateral lobes. Petals fused or free: Fused. Dimensions: Overall length 9 mm, width 7 mm, height 11 mm. Shape of tube: Funnelform. Dimensions: Length of tube 3 mm, width of tube 2 mm. Color of outer surface of tube: White N155A. Length of upper lobe: 5 mm. Width of upper lobe: 2 mm. Shape of upper lobe: Broad elliptic. Shape of tip of upper lobe: Deeply bifid, margins revolute. Color of outer surface of upper lobe: Between Violet-Blue 91B and 91C. Color of inner surface of upper lobe: Violet-Blue 90D. Length of lower lobe: 8 mm. Width of lower lobe: 8 mm. Shape of lower lobe: Broad-oblong in distal part with two triangular lobes toward the base, margins waved. Shape of tip of lower lobe: Emarginate. Color of outer surface of lower lobe: Violet-Blue 94C with an ill-defined central band of White N155A. Color of inner surface of lower lobe: Between Violet-Blue 94B and 94C with a central band of White N155A narrowly bordered with Violet N88B. Surface: Smooth.

Reproductive organs:

*Stamens.*—Number 2.

*Anther dimensions.*—Length 1 mm, width <0.5 mm.

*Anther color.*—Violet 86A.

*Pollen color.*—Nearest White N155A.

*Pollen quantity.*—Sparse to moderate.

*Filament dimensions.*—Length 7 mm, width <0.5 mm.

*Filament color.*—Violet N87D.

*Stigma position relative to stamens.*—Superior.

*Stigma.*—Indistinguishable from style.

*Style shape.*—Curved.

*Style dimensions.*—Length: 8 mm, diameter <0.5 mm.

*Style color.*—Violet N87D.

*Ovary position.*—Superior.

*Ovary shape.*—Divided into 4 spherical lobes, each measuring approximately 1 mm across in diameter.

*Ovary color.*—Yellow-Green 146D.

Seed:

*Approximate quantity produced.*—4 seeds per flower.

*Shape.*—Ovoid.

*Color.*—Brown 200D with a large hilum colored Greyed-White 156A.

*Dimensions.*—1.5 mm in length, 1.0 mm in diameter.

It is claimed:

1. A new and distinct variety of *Rosmarinus* plant named 'ROMAN BEAUTY' as illustrated and described herein.

* * * * *